United States Patent [19]

Birring

[11] Patent Number: 4,586,199
[45] Date of Patent: May 6, 1986

[54] ELASTIC PANTS

[75] Inventor: Mats G. Birring, Gothenburg, Sweden

[73] Assignee: Molnlycke AB, Gothenburg, Sweden

[21] Appl. No.: 455,033

[22] Filed: Dec. 21, 1982

[51] Int. Cl.[4] .............................................. A41B 9/00
[52] U.S. Cl. ..................................................... 2/401
[58] Field of Search ..................... 2/401; 604/397, 398

[56] References Cited

U.S. PATENT DOCUMENTS

| | | |
|---|---|---|
| 2,008,118 | 7/1935 | Waterman ................................ 2/401 |
| 2,459,043 | 1/1949 | Owenby et al. ......................... 2/401 |
| 2,956,564 | 10/1960 | O'Hara . |
| 3,322,120 | 5/1967 | Wyss et al. .............................. 2/401 |
| 3,599,640 | 8/1971 | Larson . |

FOREIGN PATENT DOCUMENTS

| | | |
|---|---|---|
| 1070779 | 12/1959 | Fed. Rep. of Germany . |
| 1203705 | 10/1965 | Fed. Rep. of Germany . |
| 1117957 | 5/1956 | France . |
| 2184543 | 12/1973 | France . |
| 2241645 | 3/1975 | France . |
| 1040053 | 8/1966 | United Kingdom . |
| 1470248 | 4/1977 | United Kingdom . |

Primary Examiner—Doris L. Troutman

[57] ABSTRACT

Elastic pants or briefs for holding a disposable diaper in place, provided in both the front and back piece with elastic threads which define a central portion tapering towards the crotch of the pants, and/or with a central area extending up from the crotch portion, which is more loosely crocheted or knitted than the rest of the pants, thereby achieving effective tightening of the underlying disposable diaper against the body of the user.

4 Claims, 7 Drawing Figures

ELASTIC PANTS

The present invention relates to elastic pants or briefs made of an elastic material and designed for holding a disposable diaper in place and consisting of a front and a back knitted or crocheted piece, which are joined to each other along their side edges and at the crotch portion of the pants.

The now common disposable diapers with tape for holding in place do not provide sufficient security against leakage. This is primarily because there are too few points of attachment, whereby gaps easily occur between the semistiff diaper and the body of the user. The problem is especially pronounced with respect to incontinent adults, who of course want to be able to get about without the risk of urine leakage for example.

The use of separate pants or briefs for holding a diaper in place is of course greatly superior to diapers with tape as regards security against the diaper coming loose or sliding out of position. Despite this, the fact that the known briefs or pants for diapers are equally elastic everywhere, with the possible exception of the waist and leg edge portions, presents particular and hitherto unsolved leakage problems. Due to the different shapes of the human body and the diaper, the pressure exerted by the known briefs or pants will be greatest along the side of the user and at the middle of the diaper. The fixing of the diaper will thus be poor and the pressure against the side edges of the diaper will be minimal, resulting in the risk of leakage particularly at the edges. Thus no completely satisfactory aid for incontinent people has been available. Since incontinence is common and quite a problem especially for significant numbers of elderly people, the facts discussed here involve a social problem of major proportions. A number of studies have shown that many people become socially isolated due to incontinence. Many do not even venture outside the home to make necessary purchases for fear of urinating. For the same reasons, all normal social intercourse is ruled out.

In short, these social problems are a result of the fact that incontinent adults have, up to now, had to live with the feeling that they cannot depend on the aids used to provide satisfactory protection.

The present invention is the first to provide a solution to these problems which is satisfactory in all respects.

The invention has achieved a pair of elastic pants, which holds the diaper in place and increases the pressure against its edges. The major feature of the pants according to the invention is that the knitting or crocheting is looser in a central area in the front and back pieces, said area extending up from the crocheted portion, and/or that elastic threads are knitted in or crocheted in to define a central portion of the front and back pieces, whereby, when the pants are used to hold a diaper in place, the defining edges of the more loosely knitted or crocheted areas and/or the elastic threads press substantially against the edges of the diaper providing an effective seal against leakage.

The invention will now be explained in the following with reference to examples, which are shown in the accompanying drawings.

Figure 1:
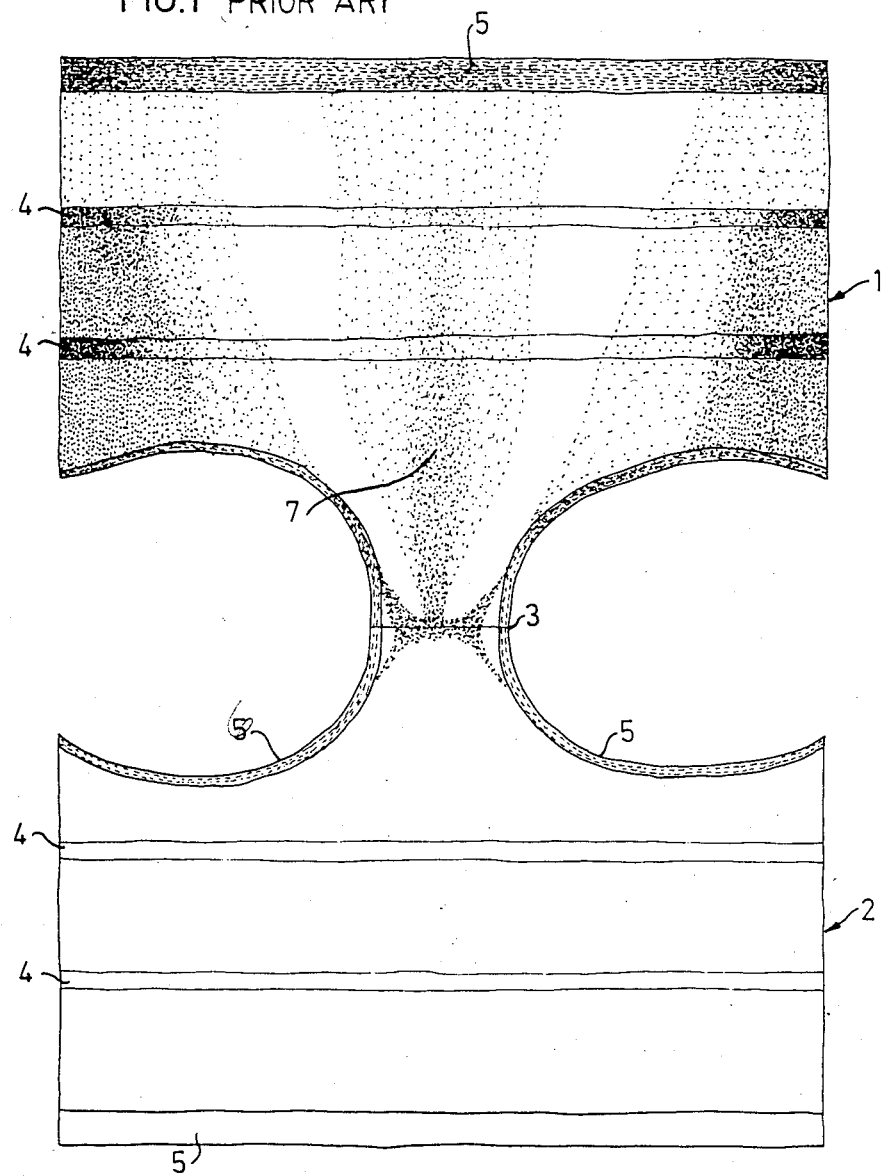
FIG. 1 illustrates the distribution of the pressure which previously known elastic pants exert against the underlying disposable diaper and the user.

FIG. 1 shows the blank of a pair of elastic pants or briefs of previously known type consisting of a front and a back piece 1,2, which are entirely identical and designed to be joined to each other along their side edges and at the crotch portion 3. The pants consist of crocheted pieces of an elastic material. Threads 4 of spandex are crocheted into the pants, but except for these and the waist bands 5 and the leg bands 6, the pants have the same elasticity everywhere. After putting the pants on over a disposable diaper, the pressure distribution illustrated in FIG. 1 is produced, where the darkest areas indicate the areas of greatest pressure.

It is easy to see that the pressure distribution resulting from the pants in FIG. 1 on an underlying diaper is entirely unsuitable. The pressure is greatest at 7, i.e. against the middle of the underlying disposable diaper, while it is least and almost non-existent at the light V-shaped area in the Figure, which covers the edge portions of the underlying diaper. Thus when the pants according to FIG. 1 are used, no edge pressure whatsoever is produced against the underlying diaper, which means that the risk of edge leakage will be especially great. Since the pressure is substantially exerted against the center of the disposable diaper, its position will not be stable and it can easily slide to one side. Furthermore, it is apparent that the pants provide poor containment of excrement, and when used by incontinent males, it also provides poor positioning of the penis which also substantially increases the risk of leakage.

Figure 2:
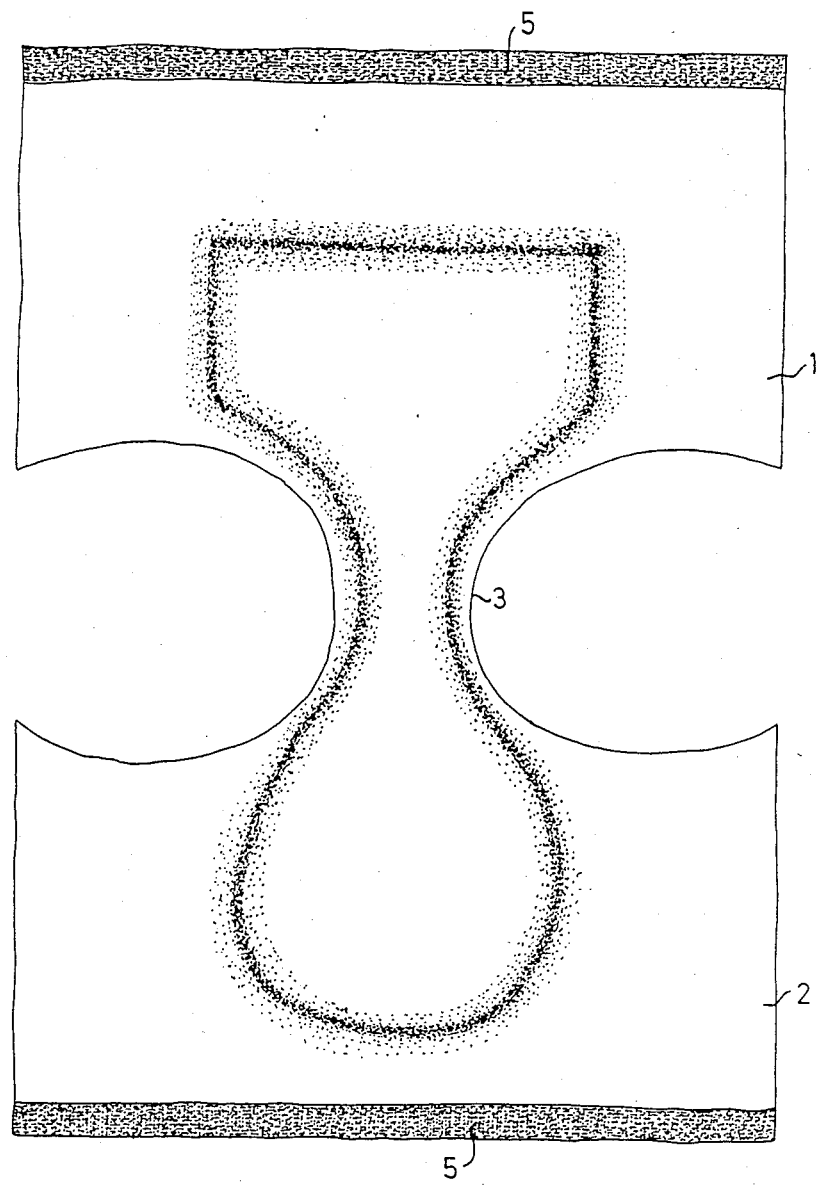
FIG. 2 shows the desired ideal pressure distribution.

The present invention, however, is based on the insight that the pressure exerted by the elastic pants or briefs against an underlying disposable diaper should have a distribution of essentially the appearance shown in FIG. 2. This pressure distribution holds the diaper firmly in the correct position, provides increased pressure along the edges of the diaper and reduced pressure across the central portions, thus together providing effective enclosure of both urine and excrement within the area covered by the disposable diaper.

Figure 3:
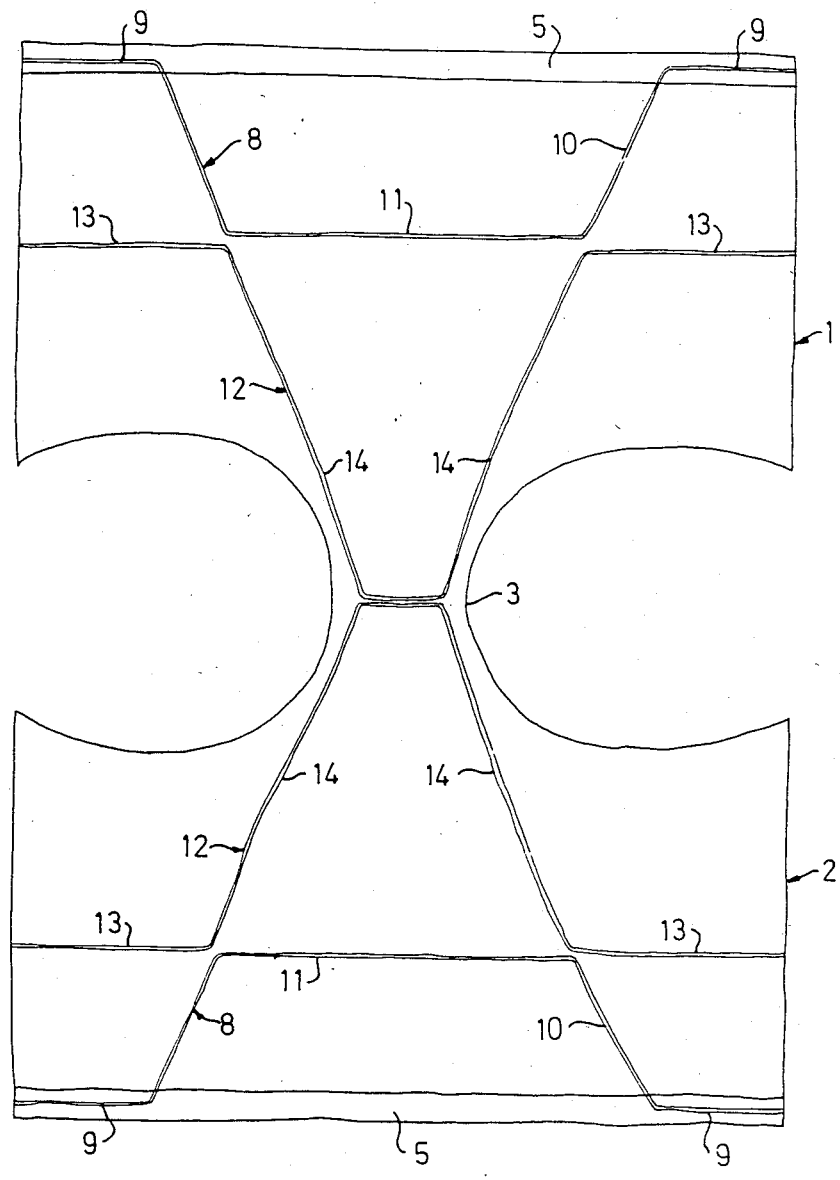
FIG. 3 shows a first embodiment of a pair of diaper pants according to the invention.

The elastic diaper according to the invention shown in FIG. 3 consists of a front and a back piece 1 and 2, respectively, of crocheted elastic material. These pieces are essentially evenly crocheted over their entire surfaces. The two pieces 1,2 are thus entirely identical. For the purpose of providing a pressure distribution of at least essentially the type shown in FIG. 2 against an underlying disposable diaper, a number of elastic threads have been crocheted into each piece, for example of spandex yarn. The elastic threads in each piece consist of a first thread 8, which extends a distance 9 from each side edge along the waist edge portion and thereafter a distance 10 diagonally inwards towards the crotch portion 3 to finally extend over a portion 11 across the central portion of the pants parallel to the waist edge; and of a second thread 12 which extends with portions 13 from the respective side edge level with the central portion 11 of the first thread 8 up to said thread and thereafter with portions 14 converging towards the crotch portion.

Figures 4, 5:
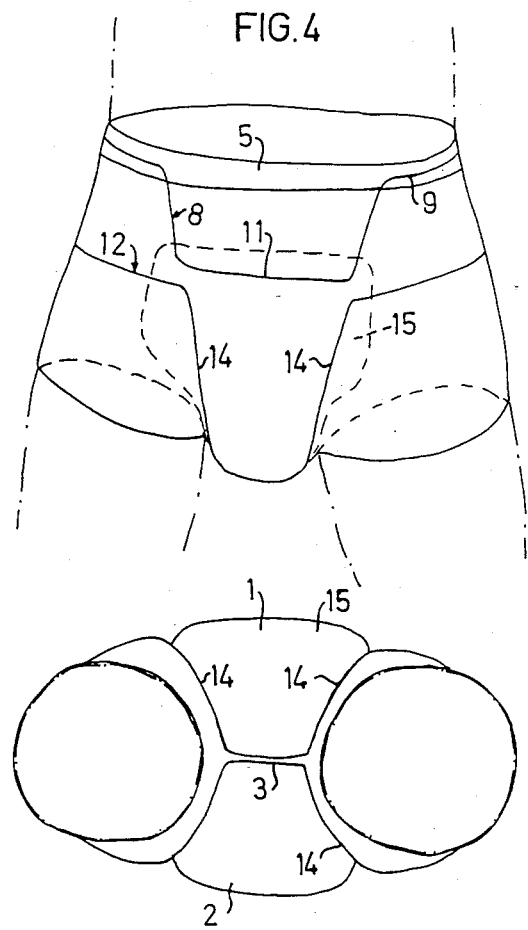
FIGS. 4 and 5 show the pants according to FIG. 3 when used to hold a disposable diaper in place.
Figure 6:
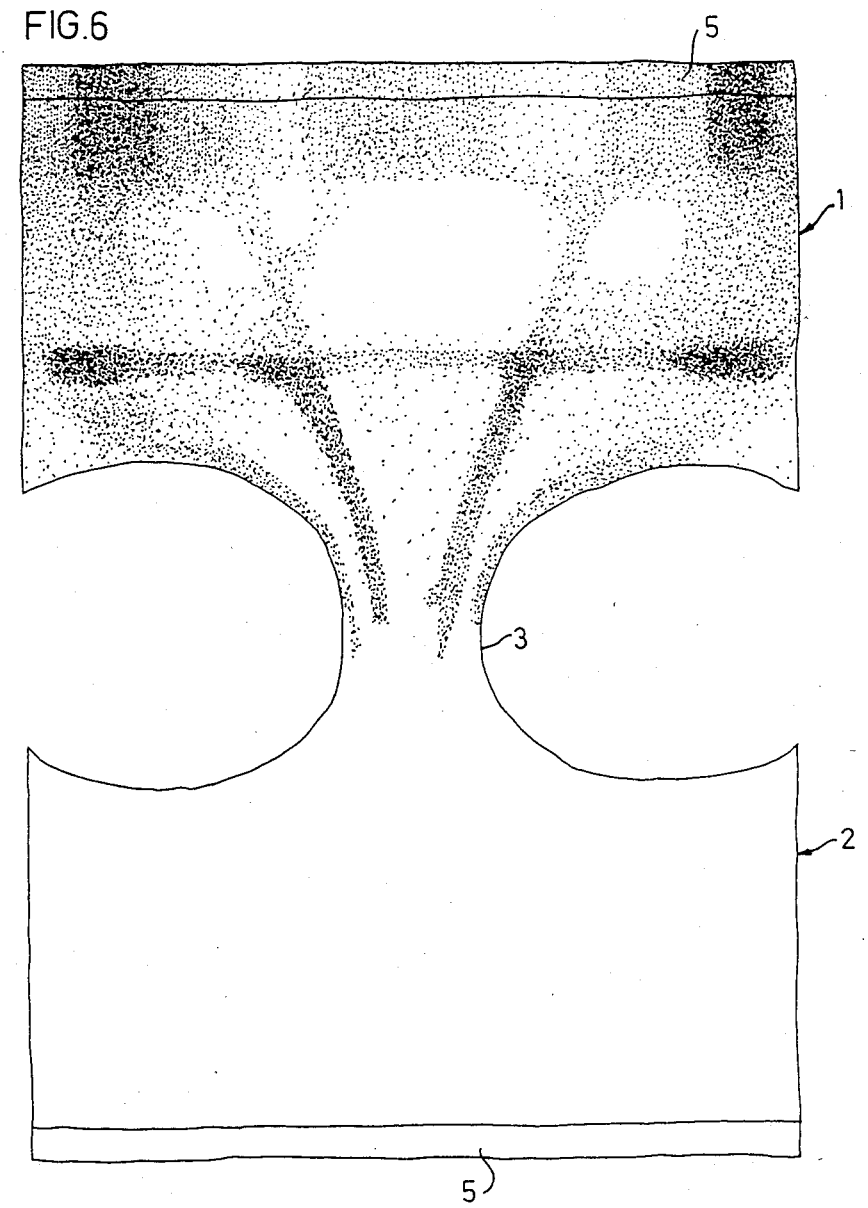
FIG. 6 shows the pressure exerted by the pants according to FIGS. 3–5 against the underlying disposable diaper and the user. Finally.

FIG. 4 shows the appearance of the pants according to FIG. 3 when used for supporting an essentially T-shaped disposable diaper 15. The central portion 11 of the first elastic thread and the portions 14 of the second elastic thread converging towards the crotch portion 3 press the side edge portions of the diaper and a horizontal portion in the vicinity of the upper end of the diaper into tight contact against the body of the user. The back of the diaper is also tensioned correspondingly. FIG. 5 shows in a view from below how the edge portions of the disposable diaper 15 are pressed against the user. The pressure distribution caused by the pants according to FIG. 3 against the underlying disposable diaper and against the user is shown in FIG. 6. A comparison of the pressure distributions according to FIGS. 1 and 2 shows that the pressure distribution caused by the elastic threads in the embodiment shown in FIG. 3 of a pair of pants according to the invention is nearly ideal.

Figure 7:
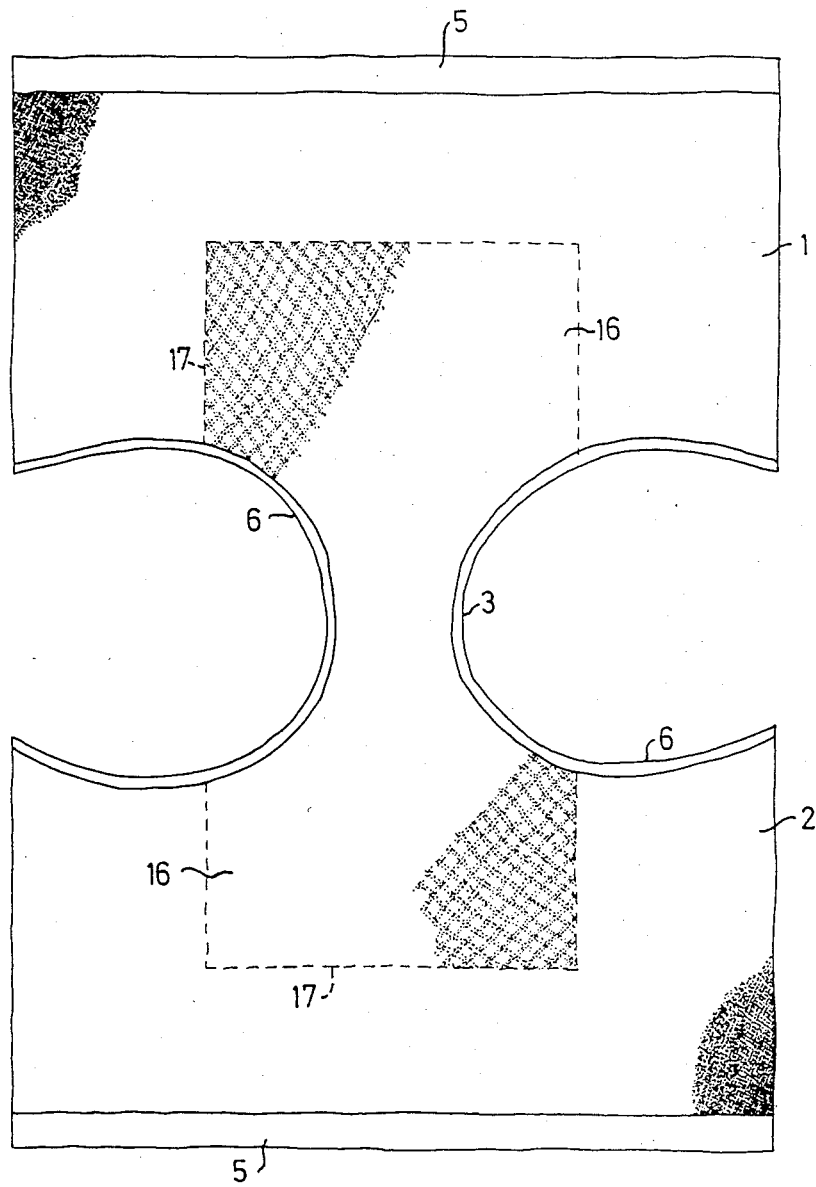
FIG. 7 shows a second embodiment of a pair of pants according to the invention.

Finally, FIG. 7 shows a further embodiment of the elastic pants according to the invention. No elastic threads have been knitted or crocheted in. Rather, a central area 16 has been crocheted looser than the rest of the pants. Thus when the pants according to FIG. 7 are used, the pressure exerted will be very little against the middle of an underlying disposable diaper, while at the boundaries between the tighter and looser crocheted areas of the pants, i.e. along the edges marked with dashed lines 17 in FIG. 7, it will be substantially greater. Effective sealing against leakage is thus obtained and the pressure exerted by the pants will be essentially ideal, i.e. essentially agreeing with the pressure distribution shown in FIG. 2.

The invention is not, however, limited to the embodiments described above. Rather, a number of modifications are possible within the scope of the following claims. The elastic threads need not of course be arranged exactly as described in connection with FIG. 3. What is important is that they produce a pressure distribution against the underlying disposable diaper of at least essentially the appearance in FIGS. 2 and 6.

Suitably, the elastic threads can be arranged as in FIG. 3, combined with a looser crocheted or knitted central area as according to FIG. 7.

The elastic pants according to the invention have been described here in connection with the use of diapers by incontinent adults. The pants in question are, however, of course also suitable for children.

What I claim is:

1. Elastic pants adapted to hold a diaper in place against the body of a user, the elastic pants being made of an elastic material having a waisted crotch portion joining a front portion of the pants to a rear portion of the pants, the front and rear portions having side edges and waist edges and each having a central portion spaced a substantial distance from said side and waist edges, and means bordering said central portion and exerting greater pressure toward the body of the user than do the central portions when the pants are in use.

2. Elastic pants as claimed in claim 1, in which said bordering means comprise elastic threads.

3. Elastic pants as claimed in claim 2, in which said elastic threads in each of said front and rear portions converge in a direction toward said crotch portion.

4. Elastic pants as claimed in claim 1, in which said elastic material is crocheted, and in which said bordering means comprises material that is crocheted tighter than the material of said central portions.

* * * * *